US011752081B2

(12) United States Patent
Wieder et al.

(10) Patent No.: US 11,752,081 B2
(45) Date of Patent: Sep. 12, 2023

(54) EMULSIFIER-FREE SUNSCREEN GEL COMPOSITION WITH TRANSPARENT APPLICATION

(71) Applicant: L'OREAL, Paris (FR)

(72) Inventors: Noah Louis Wieder, Linden, NJ (US); Paula Cziryak, Eatontown, NJ (US); Mark Zaw, Denville, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/399,107

(22) Filed: Apr. 30, 2019

(65) Prior Publication Data
US 2020/0345605 A1    Nov. 5, 2020

(51) Int. Cl.
| | | |
|---|---|---|
| *A61K 8/44* | (2006.01) | |
| *A61K 8/04* | (2006.01) | |
| *A61K 8/37* | (2006.01) | |
| *A61K 8/39* | (2006.01) | |
| *A61K 8/81* | (2006.01) | |
| *A61Q 17/04* | (2006.01) | |

(52) U.S. Cl.
CPC ............... *A61K 8/44* (2013.01); *A61K 8/042* (2013.01); *A61K 8/37* (2013.01); *A61K 8/39* (2013.01); *A61K 8/8152* (2013.01); *A61Q 17/04* (2013.01); *A61K 2800/30* (2013.01)

(58) Field of Classification Search
CPC ..................................................... A61Q 17/04
See application file for complete search history.

(56) References Cited

U.S. PATENT DOCUMENTS

| | | | |
|---|---|---|---|
| 2011/0195036 A1* | 8/2011 | Clemente ............... | A61Q 17/04 424/59 |
| 2013/0004441 A1* | 1/2013 | Bui ........................ | A61K 8/892 424/59 |
| 2015/0202139 A1* | 7/2015 | Friedman ............... | A61K 8/893 424/60 |
| 2015/0257996 A1* | 9/2015 | Howell ................... | A61K 8/042 424/401 |
| 2016/0303004 A1 | 10/2016 | Ma et al. | |
| 2019/0015315 A1* | 1/2019 | Zanatta .................... | A61K 8/87 |
| 2020/0188293 A1* | 6/2020 | Bingham ................. | A61K 8/31 |

FOREIGN PATENT DOCUMENTS

| | | |
|---|---|---|
| WO | 2016198581 A1 | 12/2016 |
| WO | 2018145831 A1 | 8/2018 |

OTHER PUBLICATIONS

Aristoflex AVC, Clariant, Product fact sheet, May 2013.*
Mintel: Julep No Excuses Invisible Sunscreen Gel for Face Broad Spectrum SPF 40; www.gnpd.com.
Mintel: Glossier Invisible Shield Daily Sunscreen +SPF 35; www.gnpd.com.
PCT Notification of Transmittal of the International Search Report and the Written Opinion of the International Searching Authority, issued to Application No. PCT/US2020/029279 dated Aug. 17, 2020.

* cited by examiner

*Primary Examiner* — Gina C Justice
(74) *Attorney, Agent, or Firm* — McNees Wallace & Nurick LLC

(57) ABSTRACT

An emulsifier-free sunscreen composition includes a suspension of oil phase droplets in a gellified water phase, the oil phase droplets including a UV filter system present from at least about 20% by weight of the composition and including one or more oil soluble UV sun filters, an amino acid gelling agent and optionally at least one diol all of which oil phase components can be blended at a temperature that is below 100 degrees C.

20 Claims, No Drawings

EMULSIFIER-FREE SUNSCREEN GEL COMPOSITION WITH TRANSPARENT APPLICATION

FIELD

The present disclosure is directed to skin care compositions that provide UV protection.

BACKGROUND

The photoprotection of keratinous substrates, including both skin and hair, is considered by many to be necessary in order to facilitate protection from sun-damage, sunburn, photo-aging, as well as to decrease the chances of skin cancer development caused by exposure to ultraviolet ("UV") radiation.

It is an object of the present disclosure to provide a composition, in particular a sunscreen composition, that provides SPF protection employing a UV filter system and that is formulated for aesthetically pleasing application to the skin that is free of emulsifiers and is clear upon application, stays clear when wet, and has improved water-resistance. Yet another object of the present disclosure is to provide a sunscreen composition that includes gellified oil and water phases allowing stabilization of the oil phase in the water phase and avoidance of a greasy feel upon application.

SUMMARY

The disclosure provides, in various embodiments, an emulsifier-free sunscreen composition. In a first exemplary embodiment, the composition includes a suspension of oil phase droplets in a gellified water phase, the oil phase droplets including a UV filter system present from at least about 20% by weight of the composition and including one or more oil soluble UV sun filters, an amino acid gelling agent and optionally at least one diol, all of which oil phase components can be blended at a temperature that is below 100 degrees C. In accordance with some embodiments, the composition further includes in the water phase at least one thickener.

In accordance with some embodiments, the amino acid gelling agent comprises one or more of dibutyl lauroyl glutamide, dibutyl ethylhexanoyl glutamide.

In accordance with some embodiments, the composition includes in the UV filter system UV sun filters selected from octocrylene, octisalate, homosalate, avobenzone, oxybenzone, mexoryl xl, and combinations of these.

In accordance with some embodiments, the composition includes at least one additive selected from hydrating agents, powders, silicone polymers, and SPF boosters. In some specific embodiments, the composition includes one or more hydrating agents that may include glycerin and one or more silicone polymers that may include one or more of dimethicone and a silicone elastomer.

In another exemplary embodiment, the composition includes a suspension of oil phase droplets in a gellified water phase, the oil phase droplets comprising a UV filter system present from at least about 20% to about 30% by weight of the composition and comprising one or more oil soluble UV sun filters, and an amino acid gelling agent present from about 0.5% to about 3.0% by weight, and at least one diol. In some embodiments, the diol is present from about 0.5% to about 3.0% by weight based on the weight of the composition, wherein the oil phase components can be blended at or below 90 degrees C. In certain embodiments, the diol is present in an amount that is not greater than about 3.0% by weight.

In accordance with embodiments that comprise at least one diol, the at least one diol comprises pentylene glycol, butylene glycol, hexylene glycol or a combination of these. As described herein, the diol facilitates solvation of the amino acid based gelling agent. As further described herein, in the various embodiments, the diol is present within the range of weight percent based on the total weight of the composition. In some such embodiments, in accordance with the disclosure, particularly desirable results may be achieved when the diol is present in the oil phase within the ranges of ratio of a UV filter to diol, based on weight. Some specific examples of the weight ratio of UV filter to diol wherein the UV filter is one of octisalate and octocrylene, are set forth herein below.

In some embodiments, the UV filter system includes octisalate, and the ratio of octisalate to diol is in the range from about 1.3:1 to about 3.3:1 octisalate:diol by weight. In a particular embodiment, the UV filter system includes octisalate, and the ratio of octisalate to diol is in the range from about 3.3:1 octisalate:diol by weight.

In other embodiments, wherein the UV filter system includes octocrylene and octisalate, and the diol is pentylene glycol, the ratio of pentylene glycol to octocrylene to octisalate may be, for example, about 1.5:5.5:5 pentylene glycol:octocrylene:octisalate.

In accordance with embodiments that comprise at least non-emulsifying thickener in the water phase, the thickener is selected from one or more of natural gums and synthetic polymers. In some such embodiments, the thickener is one or more of xanthan gum, hydroxypropyl guar, *Ceratonia siliqua* (carob) gum, ammonium polyacryloyldimethyl taurate, ammonium acryloyldimethyltaurate/steareth-25 methacrylate crosspolymer, polyacrylate crosspolymer-6, and carbomer.

In a particular embodiment the composition is an essentially homogeneous suspension of gellified oil phase droplets in a gellified water phase, the suspension comprising:
  a) an oil phase, comprising:
    i. a UV filter system comprising at least one UV sun filter, the UV filter system present from about 20% to about 30% by weight based on the weight of the composition; and
    ii. at least one amino acid gelling agent, present from about 0.5% to about 3.0% by weight based on the weight of the composition;
  b) a water phase, comprising;
    i. water, present from about 55% to about 65% by weight based on the weight of the composition; and
    ii. one or more thickeners, present from about 0.75% to about 1.50% by weight based on the weight of the composition wherein the composition is essentially free of emulsifiers, and wherein the oil phase components can be blended at a temperature that is below 100 degrees C.

In such embodiments, the composition further may include one or more of a silicone polymer and a hydrating agent, and the UV filter system comprises UV sun filters selected from octocrylene, octisalate, homosalate, avobenzone, oxybenzone, mexoryl xl, and combinations of these, the amino acid gelling agent comprises dibutyl lauroyl glutamide, the at least one non-emulsifying thickener comprises one or a combination of xanthan gum and ammonium acryloyoyldimethyltaurate/VP copolymer. In some such embodiments, wherein the UV filter system includes octisalate, the ratio of octisalate to diol is in the range from about 1.3:1 to about 3.3:1 octisalate:diol by weight.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

"Keratinous substrate" and "keratinous tissue" each includes but is not limited to skin, hair, and nails.

"Cosmetically acceptable" means a carrier that is compatible with any keratinous substrate.

"Emulsifier Free" means compositions that lack or are essentially free of an emulsifier. Some specific but non-limiting examples of emulsifiers that are lacking from the compositions include PEG-100 STEARATE, PEG-20 STEARATE and other esters of poly(ethylene glycol); SUCROSE STEARATE and other emulsifiers based on sugar esters; GLYCERYL STEARATE or other glycerol esters; DIS ODIUM ETHYLENE DICOCAMIDE PEG-15 DISULFATE, SODIUM STEROYL GLUTAMATE and other fatty amides; STEARETH-100 and other fatty ethers; ACRYLATES/C10-30 ALKYL ACRYLATE CROSSPOLYMER and similar polymeric emulsifiers; and combinations of these.

"SPF booster" refers to a material which increases the UV absorption of another material when the two are intermixed in a composition by refracting UV radiation, thereby increasing the effective path length of the UV radiation through the composition.

All SPF and UV-A ratings are provided on the basis of in-vivo value unless otherwise indicated.

The disclosure provides, in various embodiments, an emulsifier-free sunscreen composition that includes a suspension of oil phase droplets in a gellified water phase, the oil phase droplets including a UV filter system present from at least about 20% by weight of the composition and including one or more oil soluble UV sun filters, an amino acid gelling agent and optionally at least one diol, all of which oil phase components can be blended at a temperature that is below 100 degrees C. In accordance with some embodiments, the composition further includes in the water phase at least one thickener. In certain embodiments, the composition includes at least one diol present from about 0.5% to about 3.0% by weight based on the weight of the composition. Unexpectedly, such compositions demonstrate that the oil phase components can be blended at or below 90 degrees C.

Prior art compositions that include UV filters in an oil phase typically employ at least two gelling agents and high amounts of oil in order to solubilize the UV filters and the gelling agents to form the oil phase. Such formulations suffer from employing limited amounts of sunscreen in order to maintain solubility, thus minimizing the potential SPF benefit. Those which employ less oil and greater amounts of gelling agents are typically formulated at relatively high temperatures, often in excess of 100 degrees Celsius, in order to solubilize the UV filters and gelling agents. High temperatures can degrade the efficacy of UV filters, particularly organic filters. Further, in order to maintain dispersion of the oil phase in emulsion type compositions, the compositions typically include one or more emulsifiers such as emulsifying surfactants. These components can be associated with unwanted whitening upon application, and with skin drying and irritation and overall loss of skin hydration.

According to the disclosure, the inventive compositions overcome the shortcomings of the prior art and provide unexpected benefits that include high amounts of solubilized UV filters in the absence of oils, an oil phase in the form of gellified droplets suspended in a gellified water phase that is stable and remains dispersed in the absence of emulsifying surfactants, and which is clear upon application and when wet with good water resistance. Further, embodiments that employ at least one diol in the oil phase demonstrate unexpected solubility of the gelling agent in the oil phase at temperatures that are well below 100 degrees Celsius and as low as from 85 degrees to 90 degrees Celsius. The compositions include in some embodiments hydrating agents along with thickening agents in the water phase to provide a gellified water phase that imparts hydration that is statistically significantly improved over time as compared with hydrating of untreated skin. These benefits are achieved after one application of the composition.

Thus, compositions in accordance with the disclosure are free of emulsifiers, are formulated to provide clear and aesthetically pleasing application to the skin with a non-greasy feel, provide SPF protection employing a high content UV filter system, provide beneficial hydration and water-resistance, and remain clear when wet.

Oil Phase

Amino Acid Gelling Agent

The oil phase present in the composition according to the disclosure includes at least one amino acid gelling agent. An amino acid gelling agent may be selected from dibutyl lauroyl glutamide and dibutyl ethylhexanoyl glutamide. In some embodiments, inclusion of a diol with the oil phase components, as further described herein, effects an enhancement of the solubility of the oil phase components, and in particular reduces the temperature at which the amino acid gelling agent can be solubilized, thus providing a composition in which the oil phase components can be blended at or below 90 degrees C.

In some representative embodiments, an amino acid gelling agent comprises dibutyl lauroyl glutamide.

More generally, the amino acid gelling agent may be selected from a derivative of a N-acyl amino acid, as set for in U.S. Pat. No. 5,843,194, including one of the n-acyl amino acid derivatives selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof; more preferred, is n-lauroylglutamic acid dibutyl amide, n-stearyl-glutamic acid dihexyl amide, and mixtures thereof.

In accordance with the various embodiments, the amount of amino acid gelling agent present in the compositions can range from about 0.5% to about 3%, or from about 0.8% to about 2.5%, or from about 1% to about 2%, or any suitable combination, sub-combination, range, or sub-range thereof by weight, based on the weight of the composition. One of ordinary skill in the art, however, will appreciate that other ranges are within the scope of the invention.

Thus, the one or combination of amino acid gelling agent in the composition may be present by weight, based on the total weight of the composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, to about 3.0 percent, including increments and ranges therein and there between.

UV Filter System

The oil phase present in the composition according to the disclosure includes at least one, and in various embodiments, more than one UV sun filter. UV sun filters, active in UV-A and/or UV-B regions, used for the present invention can be water-soluble, fat-soluble or insoluble in commonly used cosmetic solvents. In some exemplary embodiments, the UV sun filters are selected from oil soluble UV sun filters. UV-A filter comprise groups of compounds which absorb light predominantly in the range of wavelengths 400 nm to 320 nm (UV-A) and UV-B filter comprise groups of compounds which absorb light predominantly in the range of wavelengths 400 nm to 320 nm 320 nm to 280 nm (UV-B). According to an embodiment of the invention, UV-A and UV-B can be two separate UV filters or they can be one UV filter with both UV-A and UV-B sun protection factor.

Examples of suitable UV filters include, but are not limited to, UV filters that are active in UV-A and/or UV-B regions, that may be water-soluble, fat-soluble or insoluble in commonly used cosmetic solvents, and may be inorganic or organic. UV-A filter comprise groups of compounds which absorb light predominantly in the range of wavelengths 400 nm to 320 nm (UV-A) and UV-B filter comprise groups of compounds which absorb light predominantly in the range of wavelengths 400 nm to 320 nm 320 nm to 280 nm (UV-B). According to an embodiment of the disclosure, UV-A and UV-B can be two separate UV filters or they can be one UV filter with both UV-A and UV-B sun protection factor.

In accordance with the disclosure, a UV filter system is present in the composition in the range from about 20% to about 30% based on the total weight of the composition.

Organic UV Filters

The compositions, according to the disclosure, may comprise at least one organic UV filter. If two or more organic UV filters are used, they may be the same or different. The organic UV filter used for the present disclosure may be active in the UV-A and/or UV-B region. The organic UV filter may be hydrophilic and/or lipophilic. The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; ÿ,ÿ-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof. Anthranilic compounds: Menthyl anthranilate, marketed under the trademark "Neo Heliopan MA" by Haarmann and Reimer. Dibenzoylmethane compounds: Butyl methoxydibenzoylmethane, marketed, in particular, under the trademark "Parsol 1789" by Hoffmann-La Roche; and isopropyl dibenzoylmethane. Cinnamic compounds: Ethylhexyl methoxycinnamate, marketed, in particular, under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate. Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer. Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex. Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino-2-hydroxybenzoyl)benzoate (UVINUL A+ by BASF). ÿ,ÿ-Diphenylacrylate compounds: Octocrylene, marketed in particular under the trademark "Uvinul N539" by BASF; and Etocrylene, marketed in particular under the trademark "Uvinul N35" by BASF. Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVTNUL T150 » by BASF. Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975. Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche. Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer. Imidazoline compounds: Ethylhexyl dimethoxybenzylidene dioxoimidazoline propionate. Bis-benzoazolyl compounds: The derivatives as described in EP-669,323 and U.S. Pat. No. 2,463,264. Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed, in particular, under the trademark "Escalol 507" by ISP, glyceryl PABA, and PEG-25 PABA, marketed under the trademark "Uvinul P25" by BASF. Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or-"Mexoryl XL" by L'Oreal. Benzoxazole compounds: 2,4-bis[5-1(dimethylpropyl)benzoxazol-2-yl-(4-phenyl)imino]-6-(2-ethylhexyl) imino-1,3,5-triazine, marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds: 1,1-dicarboxy(2,2'-dimethylpropyl)-4,4-diphenylbutadiene.

In some embodiments the organic UV filter(s) may be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,r-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl) imino-1,3,5-triazine, camphor benzylkonium methosulfate, and mixtures thereof.

Inorganic UV Filters

In some embodiments, the composition may comprise at least one inorganic UV filter. If two or more inorganic UV filters are used, they may be the same or different.

The inorganic UV filter used for the present disclosure may be active in the UV-A and/or UV-B region. The inorganic UV filter may be hydrophilic and/or lipophilic. The inorganic UV filter is, in some embodiments, insoluble in solvents, such as water, and ethanol commonly used in cosmetics.

It is in some embodiments desirable that the inorganic UV filter be in the form of a fine particle such that the mean (primary) particle diameter thereof ranges from 1 nm to 50 nm, and in some embodiments 5 nm to 40 nm, and in some embodiments 10 nm to 30 nm. The mean (primary) particle size or mean (primary) particle diameter herein is an arithmetic mean diameter.

The inorganic UV filter can be selected from the group consisting of silicon carbide, metal oxides, which may or may not be coated, and mixtures thereof. And in some embodiments, the inorganic UV filters are selected from pigments (mean size of the primary particles: generally from 5 nm to 50 nm, and in some embodiments from 10 nm to 50 nm) formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se. And in some embodiments, the inorganic UV filters are selected from titanium oxide, zinc oxide, and in some embodiments, titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes, such as beeswax, (meth)acrylic polymers, organic UV filters, and (per)fluoro compounds. It is in some embodiments desirable for the coating to include at least one organic UV filter. As the organic UV filter in the coating, a dibenzoylmethane derivative, such as butyl methoxydibenzoylmethane (Avobenzone) and 2,2'-Methylenebis[6-(2H-Benzotriazol-2-yl)-4-(1,1,3,3-Tetramethyl-Butyl) Phenol] (Methylene Bis-Benzotriazolyl Tetramethylbutylphenol) marketed as "TINOSORB M" by BASF, may be desirable.

Of course, the inorganic UV filter made of metal oxides may, before their treatment with silicones, have been treated with other surfacing agents, in particular, with cerium oxide, alumina, silica, aluminum compounds, silicon compounds, or their mixtures. The coated inorganic UV filter may have been prepared by subjecting the inorganic UV filter to one or more surface treatments of a chemical, electronic, mechano-chemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filter may be titanium oxides coated: with silica, such as the product "Sun veil" from Ikeda, and "Sunsil TIN 50" from Sunjin Chemical; with silica and with iron oxide, such as the product "Sunveil F" from Ikeda; with silica and with alumina, such as the products "Microtitanium Dioxide MT 500 SA" from Tayca, "Tioveil" from Tioxide, and "Mirasun TiW 60" from Rhodia; with alumina, such as the products "Tipaque TTO-55 (B)" and "Tipaque TTO-55 (A)" from Ishihara, and "UVT 14/4" from Kemira; with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck; with alumina and with aluminum laurate, such as the product "Microtitanium Dioxide MT 100 S" from Tayca; with iron oxide and with iron stearate, such as the product "Microtitanium Dioxide MT 100 F" from Tayca; with zinc oxide and with zinc stearate, such as the product "BR351" from Tayca; with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca; with silica, with alumina and with aluminum stearate and treated with a silicone, such as the product "STT-30-DS" from Titan Kogyo; with silica and treated with a silicone, such as the product "UV-Titan X 195" from Kemira; with alumina and treated with a silicone, such as the products "Tipaque TTO-55 (S)" from Ishihara or "UV Titan M 262" from Kemira; with triethanolamine, such as the product "STT-65-S" from Titan Kogyo; with stearic acid, such as the product "Tipaque TTO-55 (C)" from Ishihara; or with sodium hexametaphosphate, such as the product "Microtitanium Dioxide MT 150 W" from Tayca. Other titanium oxide pigments treated with a silicone are, and in some embodiments TiO2 treated with octyltrimethylsilane and for which the mean size of the individual particles is from 25 and 40 nm, such as that marketed under the trademark "T 805" by Degussa Silices, TiO2 treated with a polydimethylsiloxane and for which the mean size of the individual particles is 21 nm, such as that marketed under the trademark "70250 Cardre UF TiO2Si3" by Cardre, and anatase/rutile TiO2 treated with a polydimethylhydrosiloxane and for which the mean size of the individual particles is 25 nm, such as that marketed under the trademark "Microtitanium Dioxide USP Grade Hydrophobic" by Color Techniques.

And in some embodiments, the following coated TiO2 can be used as the coated inorganic UV filter: Stearic acid (and) Aluminum Hydroxide (and) TiO2, such as the product "MT-100 TV" from Tayca, with a mean primary particle diameter of 15 nm; Dimethicone (and) Stearic Acid (and) Aluminum Hydroxide (and) TiO2, such as the product "S A-TTO-S4" from Miyoshi Kasei, with a mean primary particle diameter of 15 nm; Silica (and) TiO2, such as the product "MT-100 WP" from Tayca, with a mean primary particle diameter of 15 nm; Dimethicone (and) Silica (and) Aluminum Hydroxide (and) TiO2, such as the product "MT-Y02" and "MT-Y-110 M3S" from Tayca, with a mean primary particle diameter of 10 nm; Dimethicone (and) Aluminum Hydroxide (and) TiO2, such as the product "SA-TTO-S3" from Miyoshi Kasei, with a mean primary particle diameter of 15 nm; Dimethicone (and) Alumina (and) TiO2, such as the product "UV TITAN Ml 70" from Sachtleben, with a mean primary particle diameter of 15 nm; and Silica (and) Aluminum Hydroxide (and) Alginic Acid (and) TiO2, such as the product "MT-100 AQ" from Tayca, with a mean primary particle diameter of 15 nm. In terms of UV filtering ability, TiO2 coated with at least one organic UV filter is more desirable. For example, Avobenzone (and) Stearic Acid (and) Aluminum Hydroxide (and) TiO2, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ". The uncoated zinc oxide pigments are, for example: those marketed under the trademark "Z-cote" by Sunsmart; those marketed under the trademark "Nanox" by Elementis; and those marketed under the trademark "Nanogard WCD 2025" by Nanophase Technologies. The coated zinc oxide pigments are, for example: those marketed under the trademark "Oxide Zinc CS-5" by Toshiba (ZnO coated with polymethylhydrosiloxane); those marketed under the trademark "Nanogard Zinc Oxide FN" by Nanophase Technologies (as a 40% dispersion in Finsolv TN, C12-C15 alkyl benzoate); those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z 1" by Shin-Etsu (ZnO coated with a silicone-grafted acrylic polymer dispersed in cyclodimethylsiloxane); those marketed under the trademark "Escalol Z100" by ISP (alumina-treated ZnO dispersed in an ethylhexyl methoxycinnamate/PVP-hexadecene copolymer/methicone mixture); those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in C12-C15 alkyl benzoate with hydroxystearic acid polycondensate). The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220". The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira. Coated inorganic UV filters are desirable, because the UV filtering effects of the inorganic UV filters can be enhanced. In addition, the coating(s) may help uniformly or homogeneously disperse the UV filters in the composition, according to the present disclosure.

In some particular embodiments, the UV Filter System includes one or more UV sun filter selected from octocrylene, octisalate (ethylhexyl salicylate), homosalate, avobenzone (butyl methoxydibenzoylmethane), oxybenzone (benzophenone-3), mexoryl xl (drometrizole trisiloxane), and combinations of these. In some exemplary embodiments the compositions include a mixture of at least two or more of the UV sun filters selected from octocrylene, octisalate (ethylhexyl salicylate), homosalate, avobenzone (butyl methoxydibenzoylmethane), oxybenzone (benzophenone-3), mexoryl xl (drometrizole trisiloxane).

In accordance with the various embodiments, the amount of each UV filter present the compositions can range from about 1% to about 15%, or from about 2% to about 12%, or from about 3% to about 10% or any suitable combination, sub-combination, range, or sub-range thereof by weight, based on the weight of the composition. One of ordinary skill in the art, however, will appreciate that other ranges are within the scope of the invention.

Thus, any one of the UV filters may be present, by weight, based on the total weight of the composition, is from about 1, 2, 3, 4, 5, 6, 7, 8, 9, 10, 11, 12, 13, 14, to about 15 weight percent, including increments and ranges therein and there between.

In accordance with the various embodiments, the total amount of UV filters present in the systems and compositions can range from about 15% to about 35% or from about 20% to about 30%, or from about 20% to about 25%, or any suitable combination, sub-combination, range, or sub-range thereof by weight, based on the weight of the composition. In some particular embodiments, the UV filters are present from at least about 15%, or from at least about 18%, or from at least about 20%, or from at least about 22%, or from at least about 24%, or from at least about 25%, or from at least about 28% by weight based on the weight of the composition. One of ordinary skill in the art, however, will appreciate that other ranges are within the scope of the invention.

Thus, the combination of UV filters present, by weight, based on the total weight of the composition, is from about 15, 16, 17, 18, 19, 20, 21, 22, 23, 24, 25, 26, 27, 28, 29, 30, 31, 32, 33, 34, to about 35 weight percent, including increments and ranges therein and there between.

Diol

The oil phase present in the composition according to the disclosure includes in some embodiments at least one diol which facilitates solvation of the amino acid based gelling agent. Thus, in some embodiments, a diol may be present from about 0.5 percent to about 3.0 percent by weight based on the weight of the composition. The at least one diol comprises pentylene glycol, butylene glycol, hexylene glycol or a combination of these. Inclusion of the diol with the oil phase components effects an enhancement of the solubility of the oil phase components, and in particular reduces the temperature at which the amino acid gelling agent can be solubilized, thus providing a composition in which the oil phase components can be blended at or below 90 degrees C.

In some representative embodiments, the at least one diol is pentylene glycol.

In certain embodiments, wherein the UV filter system includes octisalate, the ratio of octisalate to diol is in the range from about 1.3:1 to about 3.3:1 octisalate:diol by weight.

In other embodiments, wherein the UV filter system includes octocrylene and octisalate, and the diol is pentylene glycol, the ratio of pentylene glycol to octocrylene to octisalate may be, for example, about 1.5:5.5:5 pentylene glycol:octocrylene:octisalate. The diol:octisalate ratio could range from 1.5:5 to 3:5, and the octocrylene could be anything between 0 and 5.5. The ratio of pentylene glycol to octocrylene to octisalate may be in the range from about 1.5:0:5 to about 3:5.5:5.

In accordance with the various embodiments, the amount of diol present in the compositions can range from about 0.5% to about 3%, or from about 0.8% to about 2.5%, or from about 1% to about 2%, or any suitable combination, sub-combination, range, or sub-range thereof by weight, based on the weight of the composition. One of ordinary skill in the art, however, will appreciate that other ranges are within the scope of the invention.

Thus, the diol in the composition may be present by weight, based on the total weight of the composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, to about 3.0 percent, including increments and ranges therein and there between.

Aqueous Phase

In accordance with the disclosure, the aqueous phase is present in the composition and includes water present in the range from about 25% to about 60%. In some embodiments, the aqueous phase also includes one or more hydrating agent present from about 5% to about 25% by weight, all based on the total weight of the composition.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Cosmetically Acceptable Carrier

In accordance with the various embodiments, the compositions include a cosmetically acceptable carrier. The total amount of the cosmetically acceptable carrier in compositions may be from about 40% to about 80% by weight, based on the total weight of the composition.

The cosmetically acceptable carrier can include, for example, water and monoalcohols such as monohydric $C_1$-$C_8$ alcohols such as ethanol, propanol, butanol, isopropanol, isobutanol, and benzyl alcohol, and phenylethyl alcohol. In a representative embodiment, a cosmetically acceptable carrier according to the disclosure includes one or a combination of: water present from about 45% to about 65%, and one or more alcohol present from about 0% to about 15%, each present by weight based on the weight of the composition.

In some embodiments, the cosmetically acceptable carrier may comprise water present from about 55% to about 65% and a mono-alcohol present from about 2% to about 10%.

In some embodiments, the total amount of water in the composition is from about 40% to about 80%, or from about 45% to about 75%, or from about 55% to about 65%, or about 60% by weight based on the total weight of the composition.

Thus, a cosmetically acceptable carrier includes one or more components, in some embodiments selected from water and alcohols, present by weight, based on the total weight of the composition, within the specific ranges as described above, from about 2, 3, 4, 5, 6, 7, 8, 9 10, 11, 12, 13, 14, 15, 16, 17, 18, 19, 20, 25, 30, 35, 40, 45, 50, 55, 60, 65, 70, 75, 80, to about 80 percent, including increments and ranges therein and there between.

The pH of the compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as mono-ethanolamine, diethanolamine, triethanolamine, isopropanolamine or 1,3-propanediamine, or alternatively by addition of an inorganic or organic acid, advantageously a carboxylic acid, such as, for example, citric acid.

Non-Emulsifying Thickener

In accordance with the various embodiments, the emulsifier-free sunscreen compositions include at least one non-emulsifying thickener. The total amount of the at least one non-emulsifying thickener in compositions may be from about 0.1% to about 5.0% by weight, based on the total weight of the composition.

In some embodiments, the at least one non-emulsifying thickener comprises one or more of natural gums and synthetic polymers xanthan gum, hydroxypropyl guar, *Ceratonia siliqua* (carob) gum, ammonium polyacryloyldimethyl taurate, ammonium acryloyldimethyltaurate/steareth-25 methacrylate crosspolymer, polyacrylate crosspolymer-6, and carbomer In some embodiments, the at least one non-emulsifying thickener comprises one or a combination of xanthan gum and ammonium acryloyoyldimethyltaurate/VP copolymer.

In in accordance with the various embodiments, the total amount of thickener in the composition is present from about 0.1% to about 5%, or from about 0.15% to about 4%, or from about 0.2% to about 3%, or from about 0.25% to about 2%, or from about 0.5% to about 1.5%, or from about 0.75% to about 1% based on the total weight of the composition.

Thus, a thickener, if present in the composition is present by weight, based on the total weight of the composition, from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.85, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

In some particular embodiments, the compositions include one or more thickeners that include xanthan gum and ammonium acryloyoyldimethyltaurate/VP copolymer, each present within the range from about 0.2% to about 0.75% by weight based on the weight of the composition.

Hydrating Agent

In accordance with the disclosure, one or more hydrating agents may be present in the composition. The hydrating agent present in the cosmetic composition, according to the disclosure, includes, but is not limited to, one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the compositions include a hydrating agent selected from one or a combination of glycerin and caprylyl glycol.

In accordance with the various embodiments, the amount of hydrating agent present in the compositions can range from about 3% to about 25%, or from about 5% to about 20%, or from about 7% to about 15% or any suitable combination, sub-combination, range, or sub-range thereof by weight, based on the weight of the composition. One of ordinary skill in the art, however, will appreciate that other ranges are within the scope of the invention.

Thus, any one of or a combination of hydrating agent may be present, by weight, based on the total weight of the composition, is from about 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

Optional Additives

The compositions can also comprise at least one additive used in the cosmetics field which does not affect the properties of the compositions according to the invention, such as fragrances, pearlescent agents, silica, preservatives, proteins, protein hydrolysates, vitamins, panthenol, silicones, odor absorbers and coloring materials; anti-microbial components, including, but not limited to, caproyl glycine and sodium salicylate; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example *Pyrus malus* (Apple) Fruit Extract, and Aloe Barbadensis Leaf Juice Powder; citric acid, sodium chloride; neutralizing or pH-adjusting agents (e.g., triethylamine (TEA) and sodium hydroxide), and combinations thereof. Additives may also include SPF booster which may include light refracting bodies and materials that include a styrene-acrylate copolymer composition. In a further embodiment, the composition of the light refracting bodies is a latex. In one embodiment, the at least one SPF booster may be present in the composition in the amount of at least about 0.1%, at least about 0.3%, at least about 0.5%, at least about 0.7%, less than about 2%, less than about 1.5%, less than about 1.2%, and/or less than about 1%. Additives may also include silicone polymers, for example dimethicone, and dimethicone cross polymers, such as, for example, dimethicone (and) dimethicone/vinyl dimethicone crosspolymer.

Although the optional active additives are given as examples, it will be appreciated that other optional components compatible with cosmetic applications known in the art may be used.

In some particular embodiments, the composition includes one or a combination of actives and additives selected from SPF booster comprising styrene/akrylates copolymer, and a silicone polymer comprising dimethicone (and) dimethicone/vinyl dimethicone crosspolymer.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

EXAMPLES

Example 1: Inventive Compositions

The inventive compositions as set forth in Table 1, below, include water gel SPF 30 formulations (Inventive Compositions 1, 3 and 4), an invisible cooling high SPF gel (Inventive 2).

TABLE 1

Inventive Compositions

| INGREDIENT | INVENTIVE 1 | INVENTIVE 2 | INVENTIVE 3 | INVENTIVE 4 |
|---|---|---|---|---|
| Dibutyl Lauroyl Glutamide | 1 | 1 | 1 | 1 |
| Fragrance | | | 0.05 | |
| Xanthan Gum | 0.2 | 0.2 | 0.2 | 0.2 |
| Ammonium Acryloyldimethyltaurate/VP Copolymer | 0.55 | 0.55 | 0.75 | 0.75 |
| Phenoxyethanol | 0.5 | 0.5 | 0.5 | 0.5 |
| Dimethicone (And) Dimethicone/Vinyl Dimethicone Crosspolymer | 2.5 | 2.5 | 2.5 | 2.5 |
| Alcohol Denat. | 5 | 5 | 5 | 4.5 |
| Glycerin | 7 | 7 | 7 | 7 |
| Pentylene Glycol | | | | 1.5 |
| Caprylyl Glycol | 0.3 | 0.3 | 0.3 | 0.3 |
| Benzophenone-3 | | 3.86 | | |
| Butyl Methoxydibenzoylmethane | 3 | 3 | 3 | 3 |
| Ethylhexyl Salicylate | 5 | 3.21 | 5 | 5 |
| Octocrylene | 7 | 6 | 7 | 7 |
| Homosalate | 5 | 10.72 | 5 | 5 |
| Water | 62.95 | 56.16 | 62.7 | 61.75 |

Example 2: Demonstration of the Sun Protection Factor of Invisible Cooling High SPF Gel (Inventive 2)

An in vivo study was carried out to evaluate the SPF according to established procedures for testing for over-the-counter sunscreen products. The backs of healthy subjects who voluntarily were irradiated with UVA/UVB rays produced by a certified artificial light source (Xenon arc Solar Simulator) and the MED (Minimum Erythema Dose) was calculated 20±4 hours after the irradiation. The study was carried out on 10 subjects. The invisible cooling SPF gel was shown to have a mean of 63.5 and a SPF label of 60.

The Sun Protection factor is the ratio of the Minimal Erythemal Dose obtained in presence of the product (2 mg/cm$^2$) (medp) to the Minimal Erythemal Dose obtained without the product (medu). SPF=medp/medu The Minimal Erythemal Dose is defined as the quantity of energy necessary to produce the first perceptible unambiguous redness reaction with clearly defined borders, evaluated 16 to 24 hours after exposure to a solar simulator. With 5 increasing doses of UV (% progression based on the presumed SPF). The inventive compositions provide targeted SPF protection with a high content of UV filters without the use of emulsifiers and multiple gelling agents.

Example 3: Demonstration of the Sun Protection Factor of Water Gel SPF 30 (Inventive 1)

An in vivo study was carried out to evaluate the SPF according to established procedures for testing for over-the-counter sunscreen products. The backs of healthy subjects who voluntarily were irradiated with UVA/UVB rays produced by a certified artificial light source (Xenon arc Solar Simulator) and the MED (Minimum Erythema Dose) was calculated 20±4 hours after the irradiation. The study was carried out on 10 subjects. The invisible cooling SPF gel was shown to have a mean of 38.2 and a SPF label of 30. The inventive compositions provide targeted SPF protection with a high content of UV filters without the use of emulsifiers and multiple gelling agents.

Example 4: Demonstration of the Effectiveness of Inventive Sunscreen Compositions in Improving Skin Hydration A total of twenty-six (26) female subjects, ranging in age from 21-55 years (average age 41.23), were engaged in a clinical study that demonstrated the efficacy of the test product to improve skin hydration.

Inventive compositions 1 and 5 were evaluated for effect on hydration using an instrumental method. Changes in skin conductance, impedance or capacitance are used to study epidermal hydration in vivo. The measurement is made on the difference in dielectric constant; skin has a low dielectric constant and water has a high dielectric constant of 81. When skin is hydrated, conductance and capacitance increases, and impedance decreases. The measuring capacitor shows changes in capacitance according to the moisture content of the tissue. A glass lamina separates the metallic tracks in the probe head from the skin in order to prevent current conduction in the tissue. An electric scatter field penetrates the skin during the measurement and the dielectricity is determined. A Corneometer CM 825 (Courage and Khazaka, Germany) was used to measure the electrical capacitance/hydration of the skin. Three replicate measurements were taken from the treatment site and untreated (control) site at each measurement interval.

For each subject, baseline skin hydration readings by Corneometer at treatment and untreated (control) site. Following baseline measurements, approximately 2 mg/cm² of the test product was applied to the designated treatment sites, and at indicated intervals, readings were taken of treated and untreated sites.

TABLE 2

Percentage hydration over baseline

| INTERVAL AFTER TREATMENT | UNTREATED/ CONTROL | INVENTIVE 1 | INVENTIVE 5 |
| --- | --- | --- | --- |
| 15 minutes | 0.4 | 80 | 58 |
| 8 hours | 0.22 | 69 | 66 |
| 24 hours | −0.12 | 33 | 28 |
| 48 hours | −1.37 | NA | 18 |

Initial measurements showed no statistically significant difference in skin hydration value between the untreated and treated sites at baseline. Table 2 shows the results of treatment with the three indicated compositions. For each tested composition, there was a statistically significant increase (improvement) in skin hydration measurement at 15 minutes, 8 hours, and 24 hours post application when compared to baseline measurement (results shown as percentage change vs. baseline measurement). When comparing the treated vs. untreated sites, the treated sites demonstrated greater improvement in skin hydration values at the 15-minute, 8 hour, and 24 hour time points. The inventive compositions provide improved skin hydration after a single treatment at all time-points evaluated.

While the disclosure has been described with reference to a preferred embodiment, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/ combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. An emulsifier-free sunscreen composition comprising:
a suspension of oil phase droplets in a water phase, the oil phase droplets consisting of:
a UV filter system present from at least 22% by weight of the composition and comprising one or more oil soluble UV sun filters including octisalate and at least one diol present from about 1% to about 2%, the ratio of octisalate to diol in the range from about 1.3:1 to about 3.3:1 octisalate:diol, by weight based on the weight of the composition; and
only a single amino acid gelling agent;
optionally, dimethicone (and) dimethicone/vinyl dimethicone crosspolymer; and
optionally, additives selected from the group consisting of fragrances, preservatives, proteins, protein hydrolysates, vitamins, coloring materials; dimethicone; essential oils sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang ylang, and combinations thereof; and
the water phase comprising water and at least one thickener,
wherein components of the oil phase droplets can be blended at a temperature that is below 100° C., and
wherein the emulsifier-free sunscreen composition is free of butyloctyl salicylate.

2. The emulsifier-free sunscreen composition according to claim 1, wherein the UV filter system further comprises UV sun filters selected from octocrylene, homosalate, avobenzone, oxybenzone, drometrizole trisiloxane, and combinations of these.

3. The emulsifier-free sunscreen composition according to claim 1, wherein the amino acid gelling agent is selected from the group consisting of dibutyl lauroyl glutamide and dibutyl ethylhexanoyl glutamide.

4. The emulsifier-free sunscreen composition according to claim 1, wherein the amino acid gelling agent comprises dibutyl lauroyl glutamide present from about 0.5% to about 3.0% by weight based on the weight of the composition.

5. The emulsifier-free sunscreen composition according to claim 1, wherein the at least one non-emulsifying thickener comprises one or more of natural gums, synthetic polymers, xanthan gum, hydroxypropyl guar, *Ceratonia siliqua* (carob) gum, ammonium polyacryloyldimethyl taurate, ammonium acryloyldimethyltaurate/steareth-25 methacrylate crosspolymer, polyacrylate crosspolymer-6, or carbomer.

6. The emulsifier-free sunscreen composition according to claim 1, wherein the components of the oil phase can be blended at or below 90° C.

7. The emulsifier-free sunscreen composition according to claim 6 wherein the at least one diol comprises pentylene glycol, butylene glycol, hexylene glycol or a combination of these.

8. The emulsifier-free sunscreen composition according to claim 1, wherein the ratio of octisalate to diol is in the range from 1.66:1 to 3.33:1 octisalate:diol by weight.

9. The emulsifier-free sunscreen composition according to claim 1, wherein the UV filter system includes octocrylene and octisalate, and the diol is pentylene glycol, the ratio of pentylene glycol to octocrylene to octisalate being about 1.5:5.5:5 pentylene glycol:octocrylene:octisalate.

10. The emulsifier-free sunscreen composition according to claim 1, further comprising in the water phase at least one additive selected from hydrating agents, powders, silicone elastomers, and SPF boosters.

11. The emulsifier-free sunscreen composition according to claim 1, wherein the wherein the UV filter system is free of inorganic UV filter made of metal oxides.

12. A sun-care composition comprising:
homogeneous suspension of gellified oil phase droplets in a water phase, the suspension comprising:
a) an oil phase consisting of:
i. a UV filter system comprising at least one UV sun filter, the UV filter system present from 22% to about 30% by weight based on the weight of the composition;
ii. at least one diol present from about 1% to about 2% by weight based on the weight of the composition; and
iii. only a single amino acid gelling agent, present from about 0.5% to about 3.0% by weight based on the weight of the composition;
iv. optionally, dimethicone (and) dimethicone/vinyl dimethicone crosspolymer; and
v. optionally, additives selected from the group consisting of fragrances, preservatives, proteins, protein hydrolysates, vitamins, coloring materials; dimethicone; essential oils sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang ylang, and combinations thereof; and
b) the water phase, comprising;
i. water, present from about 55% to about 65% by weight based on the weight of the composition; and
ii. one or more thickeners, present from about 0.75% to about 1.50% by weight based on the weight of the composition, wherein the sun-care composition is free of butyloctyl salicylate, wherein the composition is essentially free of emulsifiers, and wherein the oil phase components can be blended at a temperature that is below 100° C.

13. The sun-care composition according to claim 12, the composition further comprising one or more of a silicone polymer and a humectant, and wherein the UV filter system comprises UV sun filters selected from octocrylene, octisalate, homosalate, avobenzone, oxybenzone, drometrizole trisiloxane, and combinations of these, the amino acid gelling agent is dibutyl lauroyl glutamide, the at least one non-emulsifying thickener comprises one or a combination of xanthan gum and ammonium acryloyldimethyltaurate/VP copolymer.

14. A sun-care composition comprising:
a) an oil phase consisting of:
   i. a UV filter system comprising at least one UV sun filter, the UV filter system present from 22% to about 30% by weight based on the weight of the composition;
   ii. only a single amino acid gelling agent, present from about 0.5% to about 3.0% by weight based on the weight of the composition;
   iii. at least one diol present from about 1% to about 2% by weight based on the weight of the composition;
   iv. optionally, dimethicone (and) dimethicone/vinyl dimethicone crosspolymer; and
   v. optionally, additives selected from the group consisting of fragrances, preservatives, proteins, protein hydrolysates, vitamins, coloring materials; dimethicone; essential oils sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang ylang, and combinations thereof; and
b) a water phase comprising;
   i. water, present from about 55% to about 65% by weight based on the weight of the composition;
   ii. one or more thickener, present from about 0.15% to about 4% by weight based on the weight of the composition,
wherein the UV filter system includes octisalate, and the ratio of octisalate to diol is in the range from about 1.3:1 to about 3.3:1 octisalate:diol by weight, and wherein the composition is essentially free of emulsifiers, and comprises a suspension of gellified oily droplets in a gellified water phase, and wherein the oil phase components can be blended at or below 90° C., and wherein the sun-care composition is free of butyloctyl salicylate.

15. The sun-care composition according to claim 14, wherein the wherein the UV filter system is free of inorganic UV filter made of metal oxides.

16. The sun-care composition according to claim 14, the composition further comprising one or more of a silicone polymer, an SPF booster and a hydrating agent, and wherein the UV filter system comprises UV sun filters selected from octocrylene, octisalate, homosalate, avobenzone, oxybenzone, drometrizole trisiloxane, and combinations of these, the amino acid gelling agent is dibutyl lauroyl glutamide, the at least one non-emulsifying thickener comprises one or a combination of xanthan gum and ammonium acryloyldimethyltaurate/VP copolymer, and the at least one diol comprises pentylene glycol, butylene glycol, hexylene glycol or a combination of these.

17. The sun-care composition according to claim 12, wherein the UV filter system includes octisalate, and the ratio of octisalate to diol is in the range from about 1.3:1 to about 3.3:1 octisalate:diol by weight.

18. The sun-care composition according to claim 12, wherein the wherein the UV filter system is free of inorganic UV filter made of metal oxides.

19. The sun-care composition according to claim 12, wherein the oil phase consists of:
the UV filter system having the at least one UV sun filter;
the at least one diol;
the single amino acid gelling agent;
dimethicone (and) dimethicone/vinyl dimethicone crosspolymer; and
one or more additives selected from the group consisting of fragrances, preservatives, proteins, protein hydrolysates, vitamins, coloring materials; dimethicone; essential oils sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang ylang, and combinations thereof.

20. The emulsifier-free sun-care composition according to claim 1, wherein the oil phase droplets consist of:
the UV filter system having the one or more oil soluble UV filers;
the at least one diol;
the single amino acid gelling agent;
optionally, dimethicone (and) dimethicone/vinyl dimethicone crosspolymer; and
optionally, additives selected from the group consisting of fragrances, preservatives, proteins, protein hydrolysates, vitamins, coloring materials; dimethicone; essential oils sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang ylang, and combinations thereof.

* * * * *